United States Patent
Daniel et al.

(10) Patent No.: US 10,357,367 B2
(45) Date of Patent: Jul. 23, 2019

(54) PATIENT-SPECIFIC MANDIBLE GRAFT CAGE

(71) Applicant: DePuy Synthes Products, Inc., Raynham, MA (US)

(72) Inventors: Steffan Daniel, Zuchwil (CH); André Furrer, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/700,904

(22) Filed: Sep. 11, 2017

(65) Prior Publication Data

US 2019/0076251 A1    Mar. 14, 2019

(51) Int. Cl.
*A61F 2/28* (2006.01)
*A61F 2/30* (2006.01)

(52) U.S. Cl.
CPC .......... *A61F 2/2803* (2013.01); *A61F 2/2846* (2013.01); *A61F 2/30771* (2013.01); *A61F 2/30942* (2013.01); *A61F 2002/285* (2013.01); *A61F 2002/3092* (2013.01); *A61F 2002/30945* (2013.01); *A61F 2002/30952* (2013.01)

(58) Field of Classification Search
CPC ............ A61F 2002/2807; A61F 2/2846; A61F 2/2803; A61F 2002/2835; A61F 2002/2842; A61F 2002/285; A61F 2/2875; A61F 2002/281; A61F 2/2889; A61F 2/3094; A61F 2/30942; A61F 2002/30943–2002/30952; A61F 2002/30962–2002/30971; A61F 2/3099; A61F 2002/30991
See application file for complete search history.

(56) References Cited

U.S. PATENT DOCUMENTS

| 3,710,789 | A | * | 1/1973 | Ersek | ................. | A61B 17/8085 |
| | | | | | | 606/281 |
| 4,820,305 | A | * | 4/1989 | Harms | .................. | A61F 2/2846 |
| | | | | | | 623/16.11 |
| 4,969,901 | A | * | 11/1990 | Binder | .................. | A61F 2/0059 |
| | | | | | | 623/17.18 |
| D326,157 | S | * | 5/1992 | Giunta | ........................ | D24/155 |

(Continued)

FOREIGN PATENT DOCUMENTS

EP         2895092        7/2015
WO       2015/138657     9/2015

*Primary Examiner* — Alvin J Stewart
(74) *Attorney, Agent, or Firm* — Fay Kaplun & Marcin, LLP

(57) ABSTRACT

A method for treating a mandible including forming an initial digital 3D model of a mesh graft containment device based on dimensions of a target space of a mandible to be filled via the graft containment device, the 3D model of the graft containment device defined via a buccal surface, a lingual surface, a superior surface and an inferior surface, individually adjusting one of the buccal surface and the lingual surface relative to a first midplane, which extends through a longitudinal axis of the graft containment device between the buccal and lingual surfaces, to add or remove bulk along a desired portion of the 3D model of the graft containment device to form an adjusted 3D model, and forming a final graft containment device for placement in the target space of the mandible based on the adjusted 3D model.

14 Claims, 2 Drawing Sheets

(56) References Cited

U.S. PATENT DOCUMENTS

| | | | | |
|---|---|---|---|---|
| 5,730,743 | A * | 3/1998 | Kirsch | A61B 17/8085 606/215 |
| 5,766,176 | A * | 6/1998 | Duncan | A61B 17/8085 606/281 |
| 5,798,924 | A * | 8/1998 | Eufinger | A61C 13/0004 700/117 |
| 6,030,218 | A * | 2/2000 | Robinson | A61C 8/0006 433/173 |
| 6,123,731 | A * | 9/2000 | Boyce | A61B 17/7062 523/113 |
| 6,277,150 | B1 * | 8/2001 | Crawley | A61F 2/0059 623/17.18 |
| 6,409,764 | B1 * | 6/2002 | White | A61C 8/0006 424/424 |
| 7,887,587 | B2 * | 2/2011 | Griffiths | A61L 31/16 623/16.11 |
| 8,485,820 | B1 * | 7/2013 | Ali | A61C 8/0027 433/173 |
| 8,945,220 | B2 * | 2/2015 | Griffiths | A61L 31/16 623/16.11 |
| 9,364,330 | B2 * | 6/2016 | Lindsey | A61B 17/68 |
| 9,925,046 | B2 * | 3/2018 | Larsen | A61F 2/2846 |
| 2002/0059049 | A1 * | 5/2002 | Bradbury | A61F 2/30942 703/11 |
| 2002/0169066 | A1 * | 11/2002 | Cassidy | A61F 2/28 501/80 |
| 2005/0015154 | A1 * | 1/2005 | Lindsey | A61B 17/68 623/23.46 |
| 2006/0129328 | A1 * | 6/2006 | Leo | A61C 13/0004 702/19 |
| 2006/0224242 | A1 * | 10/2006 | Swords | A61B 17/8085 623/17.19 |
| 2009/0253099 | A1 * | 10/2009 | Debry | A61C 8/0012 433/174 |
| 2010/0215718 | A1 * | 8/2010 | Swords | A61L 27/12 424/423 |
| 2010/0256773 | A1 * | 10/2010 | Thijs | A61C 8/0006 623/23.55 |
| 2012/0271418 | A1 * | 10/2012 | Hollister | A61F 2/28 623/17.11 |
| 2012/0296441 | A1 * | 11/2012 | Mikhail | A61F 2/2803 623/23.63 |
| 2013/0164707 | A1 * | 6/2013 | Ali | A61C 8/0027 433/173 |
| 2014/0074438 | A1 * | 3/2014 | Furrer | A61B 17/8071 703/1 |
| 2014/0364961 | A1 * | 12/2014 | Mikhail | A61F 2/2803 623/23.52 |
| 2015/0272598 | A1 * | 10/2015 | Dubois | A61B 34/10 606/280 |
| 2015/0320563 | A1 * | 11/2015 | Schwartz | A61F 2/0077 623/14.12 |
| 2015/0374497 | A1 * | 12/2015 | Engstrand | A61F 2/2846 623/17.19 |
| 2017/0014169 | A1 * | 1/2017 | Dean | A61B 34/10 |
| 2017/0216033 | A1 | 8/2017 | Daniel et al. | |
| 2017/0231767 | A1 | 8/2017 | Larsen et al. | |
| 2017/0239054 | A1 * | 8/2017 | Engstrand | A61F 2/2875 |
| 2017/0290645 | A1 * | 10/2017 | Rostami | A61C 8/0006 |
| 2017/0304056 | A1 * | 10/2017 | Gaignon | A61L 27/58 |
| 2017/0354503 | A1 * | 12/2017 | Larsen | A61F 2/2846 |
| 2018/0116802 | A1 * | 5/2018 | Daniel | A61B 17/8071 |
| 2018/0193530 | A1 * | 7/2018 | Barbas | A61F 2/28 |
| 2018/0221153 | A1 * | 8/2018 | Daniel | A61F 2/28 |
| 2018/0296343 | A1 * | 10/2018 | Wei | A61F 2/28 |

* cited by examiner

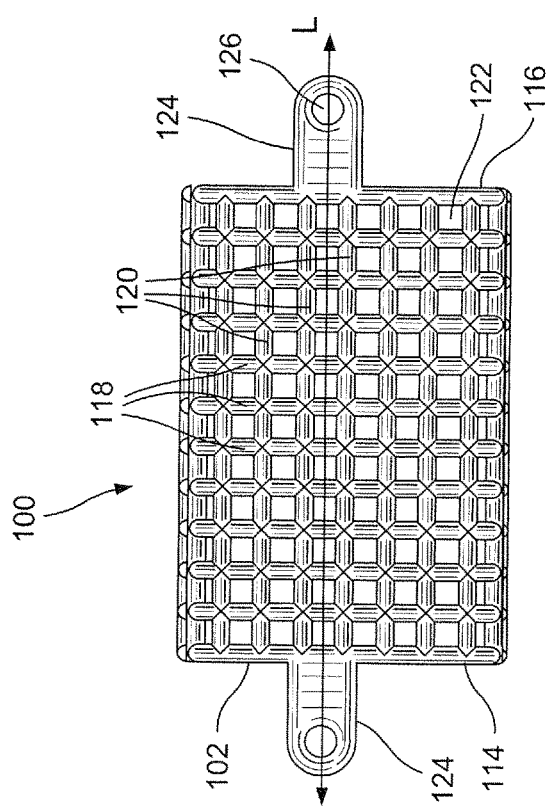
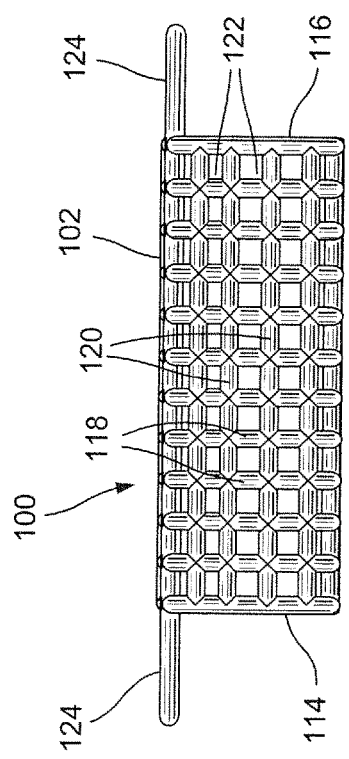
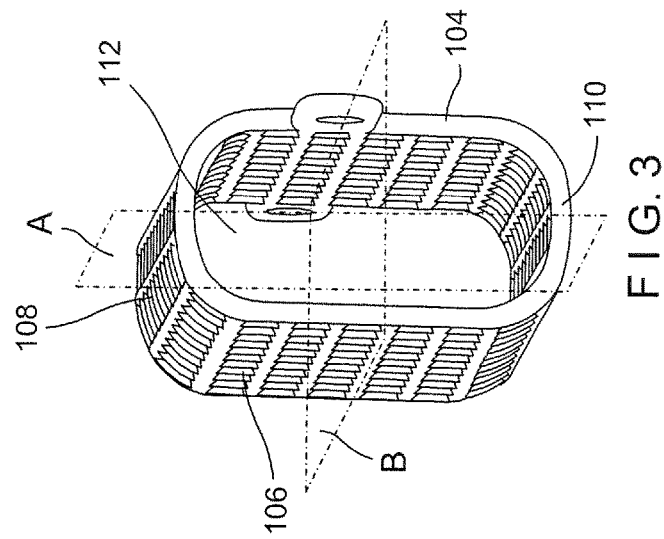

PATIENT-SPECIFIC MANDIBLE GRAFT CAGE

BACKGROUND

Mandible defects are often treated with bone grafts and/or implants such as, bone plates, to assist with healing. The bone graft material may be placed in the target area using any of a variety of methods. However, without a container for the bone graft material, the graft material may fall away from a target site before it has been incorporated by the body into the healing bone.

SUMMARY

The present embodiments are directed to a method for treating a mandible, comprising forming an initial digital 3D model of a mesh graft containment device based on dimensions of a target space of a mandible to be filled via the graft containment device, the 3D model of the graft containment device defined via a buccal surface, a lingual surface, a superior surface and an inferior surface, individually adjusting one of the buccal surface and the lingual surface relative to a first midplane, which extends through a longitudinal axis of the graft containment device between the buccal and lingual surfaces, to add or remove bulk along a desired portion of the 3D model of the graft containment device to form an adjusted 3D model, and forming a final graft containment device for placement in the target space of the mandible based on the adjusted 3D model.

The present embodiments are also directed to a graft containment device for treating a mandible, comprising a mesh body extending along a longitudinal axis from a first end to a second end and including a channel extending therethrough along the longitudinal axis, the mesh body defined via a buccal surface, a lingual surface, a superior surface and an inferior surface, dimensions of the mesh body defined via dimensions of a target area of the mandible to be filled and a desired treatment plan for the mandible, one of a distance between and a relative position of the buccal and lingual surfaces of the mesh body selected to accommodate a portion of a dental implant therein without requiring additional prosthetic elements.

BRIEF DESCRIPTION

FIG. 1 shows a side view (i.e., from a buccal side) of a device according to an exemplary embodiment of the present invention;

FIG. 2 shows a superior view of the device of FIG. 1;

FIG. 3 shows a perspective view of the device of FIG. 1.

DETAILED DESCRIPTION

Figure 4:
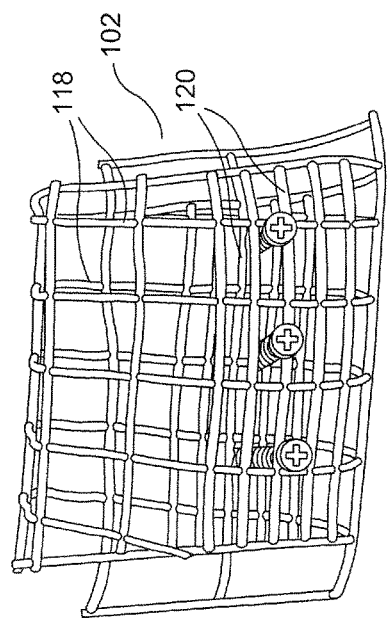
FIG. 4 shows an enlarged perspective view of a portion of the device of FIG. 1.

The present invention may be understood with reference to the following description and the appended drawings, wherein like elements are referred to with the same reference numerals. The present invention relates to the treatment of bone and, in particular, relates to treatments using bone grafts and bone graft substitutes. Exemplary embodiments of the present invention describe a patient-specific graft containment cage configured to be positioned in a gap or space in a target bone (e.g., the mandible) so that graft material may be packed therein to encourage and guide the growth of new bone into the gap/space. In one exemplary embodiment, the cage is positioned between two separated portions of bone to generate new bone joining the separated portions of bone. It will be understood by those of skill in the art, however, that the graft containment cage may be inserted or positioned within any gap or space in the target bone including, for example, at an end of the bone, so that there is bone only on one side of the graft containment cage, or within a recessed space of the bone, so that three sides of the graft containment cage contact bone, etc. Patient-specific graft cages may be formed using, for example, 3D printing, and may be based on dimensions of the patient's specific anatomy obtained via images such as, for example, CT scans or X-rays. An exemplary embodiment of the of the present invention, however, describes adjusting a buccal and lingual side of the mesh body to define a desired width (e.g., distance between buccal and lingual surfaces) of the graft containment device and/or superior and inferior sides to define a desired depth (e.g., distance between superior and inferior surfaces) of the graft containment device. The width and depth may be independently adjusted so that a lateral cross-section of the graft containment device may be specifically adjusted to provide or remove bulk along desired areas of the graft containment cage. Dimensions of the graft containment cage may be adjusted according to a desired treatment plan for the patient. In another embodiment, surfaces of the graft containment device may be dependently adjusted to adjust a trajectory (e.g., curvature) of the graft containment device while maintaining the same width and depth.

As shown in FIGS. 1-5, a graft containment device 100 according to an exemplary embodiment of the present disclosure may be custom built for a specific patient based on the patient's anatomy and a treatment plan for the patient. The graft containment device 100 comprises a body 102 extending along a longitudinal axis L and a defines a channel 112 extending therethrough along the longitudinal axis L within which graft material may be packed. The graft containment device 100 is configured to be positioned within a target space of a bone such as, for example, a mandible, and may be generally defined by a buccal surface 104, a lingual surface 106, a superior surface 108 and an inferior surface 110. Initial dimensions for a digital 3D model of the body 102 may be based upon the patient's specific anatomy. For example, a size and shape of the 3D model of the body 102 may substantially correspond to a size and shape of the target space of the mandible to be filled. Upon creation of the initial 3D model, a user (e.g., surgeon or other technician) may separately adjust a position/orientation and/or distance of the buccal surface 104 and the lingual surface 106 relative to a midplane A, which extends through the longitudinal axis L midway between the buccal and lingual surfaces 104, 106, to adjust a width of the 3D model of the body 102. The user may also separately adjust a position and/or distance of the superior surface 108 and the inferior surface 110 relative to a midplane B, which extends through the longitudinal axis L midway between the superior and inferior surfaces 108, 110, to adjust a depth of the 3D model. These surfaces 104-110 may be independently adjusted to add or remove bulk along desired portions of the body 102 to define a desired lateral cross-section of the body 102, according to the patient's treatment plan. It will be understood by those of skill in the art that although the midplanes A, B are shown as substantially planar, these midplanes may be curved along a trajectory of the cage. Adjusting surfaces 104-110 of the body 102 may include adjusting corners of the graft containment device 100 so that both a distance and a position/orientation of the surfaces 104-110 relative to the midplanes A, B may adjusted. Alternatively, each of the surface 104-110 may be adjusted to change a distance of the surfaces 104-110 from the midplanes A, B while maintaining a position/orientation of each relative to the midplanes A, B. The treatment plan may include, for example, planned future dental implants and/or measures to prevent or reduce the likelihood of soft tissue irritation, as will be described in greater detail below. Once the 3D model has been adjusted, as desired, the patient-specific graft device 100 may be printed based on the adjusted 3D model.

The body 102 extends along the longitudinal axis L from a first end 114 to a second end 116 and includes the channel 112 extending therethrough along the longitudinal axis L. The body 102 of this embodiment may be formed as a mesh including, for example, a lattice of circumferential and longitudinal members 118, 120, constructed of any suitable biocompatible material. The body 102 may be formed of, for example, a resorbable polymer such as polycapralactone, or a nonresorbable material. The circumferential and longitudinal members 118, 120, respectively, of the body 102 are spaced from one another by distances selected to form a plurality of pores 122 sized to promote vascularization of the bone while preventing graft material packed in the body 102 from falling out of the body 102. For example, pores 122 having a size greater than 0.3 mm may promote vascularization of the bone. In an alternate embodiment, the body 102 may be formed of a mesh material without discrete circumferential members 118 and longitudinal members 120, and may include pores 122 sized similarly to those formed in the device 100. As described above, the mesh material of the body 102 defines the buccal surface 104, the lingual surface 106, the superior surface 108 and the inferior surface 10. Although the body 102 is shown as having a substantially rectangular cross-section, it will be understood by those of skill in the art that the cross-section of the body 102 may have a variety of shapes so long as the shape corresponds to the target space of the bone.

In one exemplary embodiment, all of the pores 122 are substantially the same size. For example, some or all of the pores 122 may be sized and shaped to receive bone fixation elements therethrough. In another exemplary embodiment, a select number of the pores 122 may be sized and shaped to receive bone fixation elements therethrough. For example, as shown in FIG. 4, the body 102 may be formed so that, while the circumferentially members 118 are spaced substantially equidistant from one another, a distance between a portion of adjacent longitudinal members 120 may be adjusted so that the pores 122 along this adjusted portion are sized to receive bone fixation elements therethrough. In one particular example, the pores 122 sized and shaped to receive bone fixation elements therethrough may be shaped as squares with sides of approximately 1.8 mm which, as will be understood by those of skill in the art, may receive 2.4 mm bone fixation screws. In cases in which the graft containment device 100 is used with a fixation plate, bone fixation elements may be inserted through the openings of the fixation plate and through correspondingly sized pores 122 of the body 102 to fix the fixation plate relative to the graft containment device 100. It will be understood by those of skill in the art that any pore patterns specifically shown and described are exemplary only and that the graft containment device 100 may be formed with in of a variety of pore patterns, depending on desired features of the graft containment device, so long as the pores 122 are sized to permit vascularization and prevent graft material from falling therethrough.

The graft containment device 100 may also include a fixation tab 124 extending from the body 102 to fix the graft containment device 100 to the bone. The fixation tab 124 extends from at least one of the first and second ends 114, 116 of the body 102 and includes an opening 126 extending therethrough, the opening sized and shaped to receive a bone fixation element for fixing the graft containment device 100 to the bone. The fixation tab 124 may extend from the buccal surface 106 of the body 102 so that, when the graft containment device 100 is positioned within the target space of the bone the fixation tab 124 extends along a buccal surface of the mandible. Where the graft containment device 100 includes a fixation tab 124 extending from each of the first and second ends 114, 116, the fixation tab 124 extends over the separated portions of the bone which are being bridged by the graft containment device 100.

Current patient-specific graft cages are designed primarily based on the patient's anatomy. For example, a cross-section of the graft cage generally matches a cross-section of the portion of bone being replaced. As will be understood by those of skill in the art, however, portions of the mandible— particularly an anterior portion of the mandible—may have a wider base and a narrower ridge so that a lateral cross-section of the mandible tapers toward the ridge (e.g., the buccal and lingual surfaces 104, 106 taper as they extend toward the superior surface 108). Thus, placement of dental implants along graft cages designed based solely on dimensions of the target space of the anatomy requires the use of additional prosthetic elements such as rods and arches. In an example where a portion of the mandible includes a recess along a portion of a lingual surface thereof, a conventional dental implant placed on a conventional graft cage would need to be positioned further in a buccal direction than might otherwise be desired and would require additional prosthetic elements for support. Individually adjusting a position/distance of the buccal and/or lingual surfaces 104, 106 of the 3D model of the body 102 relative to the midplane A, as made possible by the present embodiments, allows the user to adjust a width of the 3D model so that bulk may be added along a desired portion (e.g., to the lingual surface along an anterior portion of the mandible) thereof.

The 3D model may be adjustable so that the width may be varied along a length of the graft containment device 100. The position/distance of the superior and/or inferior 108, 110 of the 3D model of the body 102 may also be individually adjusted to adjust the depth of the body 102. In particular, a graft containment device extending too far beyond any surface of the target space in which the graft containment device 100 is being placed may pose a risk of soft tissue irritation. To release pressure on the soft tissue, one or more of the super and/or inferior surfaces 108, 110 may be adjusted.

In some cases it may be desired to adjust a trajectory of the 3D model of the device 100 while maintaining dimensions of the width and depth of the body 102. Thus, the user may select whether to adjust the width/depth independently or dependently. When the user elects to adjust the width and/or depth independently, surfaces of the body 102 may be adjusted relative to the midplanes A, B to independently define the distances/positions of each of the surfaces 104-110 relative to the midplanes A, B. Each of the corners of the surfaces 104-110 may be adjusted to change both an position/orientation and a distance of the surfaces 104-110 relative to the midplanes A, B, as described above. When the user elects to adjust the width/depth dependently, the width and depth remain the same so that adjusting one of the surfaces 104-110 changes a trajectory of the body 102.

The user may also adjust a size and/or shape of the pores 122 of the 3D model for the body 102. In particular, a distance between adjacent circumferential and/or longitudinal members 118, 120 may be adjusted to achieve, for example, a desired functionality, along portions thereof. For example, as described above, a distance between adjacent circumferential and/or longitudinal members 118, 120 along a portion of the body 102 may be adjusted to allow bone fixation elements of different sizes to be received therein. In another exemplary embodiment, portions of the circumferential and/or longitudinal members 118, 120 may be removed along only desired portions of the body 102 to increase a pore size only along those desired portions. For example, pores 122 along a portion of the body 102 corresponding to an alveolar ridge (e.g., along the super surface 108), along which dental implants may be implanted, may be increased in size and/or specifically positioned so that a drill and/or dental implant does not come directly contact the body 102. This may reduce the risk of bacterial adhesion and infection since the drill will not be required to come into direct contact with any portion of the circumferential and/or longitudinal members 118, 120.

The fixation tab 124 may also be adjusted to extend from a desired portion of the body 102 to permit fixation of the graft containment device 100 to a desired portion of a target bone. The graft containment device 100 may be designed to include one or more fixation tabs 124 extending from any desired surface of the body 102. In one exemplary embodiment, the initial 3D model of the graft containment device 100 may be formed with two fixation tabs 124, one tab 124 extending from the buccal surface 104 at each of the ends 114, 116. In a further embodiment, the graft containment device 100 may be adjusted to include additional fixation tabs 124. For example, two additional tabs 124 may be added extending from the inferior surface 110, at each of the ends 114, 116. Once the 3D model of the graft containment device 100 has been adjusted, as desired, the 3D model is 3D printed to form the custom, patient-specific graft containment device 100.

According to an exemplary method for creating a custom, patient-specific graft containment device 100, an initial 3D model based on data including images (e.g., CT, X-ray) of the bone (e.g., the mandible) and the target space of the bone to be filled is created. Thus, the 3D model substantially matches the patient's specific anatomy. In other words, a cross-section of the 3D model substantially corresponds to the portion of the bone being replaced by the graft containment device 100. As described above, however, in many cases, it may be desired to alter the size and/or shape of the graft containment device 100 based on a patient's specific treatment plan and/or to achieve desired results. The user may adjust the width of the 3D model by individually adjusting the position/distance of the buccal surface 104 and/or the lingual surface 106 relative to the midplane A. The user may also adjust the depth of the 3D model by individually adjusting the position/distance of the superior surface 108 and/or the inferior surface 110 of the body 102 relative to the midplane B. Alternatively, or in addition, a trajectory of the body 102 of the 3D model may be adjusted. The sizes of select ones of the pores 122 may be adjusted by removing portions of circumferential and/or longitudinal members 118, 120 and/or by adjusting a distance between adjacent circumferential members 118 and/or adjacent longitudinal members 120. Thus, a shape of the graft containment device 100 may be customized to both the patient's specific anatomy and according to the treatment plan/desired result for the patient. In particular, bulk may be added and/or removed along desired portions of the 3D model to create the custom graft containment device 100.

In one exemplary embodiment, the adjustments may be made based on planned dental implants. In particular, bulk may be added along portions of the lingual surface 106 so that future dental implants may be optimally positioned along the graft containment device 100. In addition, pores 120 along the alveolar ridge (i.e., superior surface 108) may be increased in size and/or circumferential and longitudinal members 118, 120 may be specifically positioned so that the paths along which drilling is expected are open to avoid contact between the drill and the graft containment device 100. For example, portions of the circumferential and longitudinal members 118, 120 extending along the superior surface 108, which may be interfere with the placement of the dental implants may be removed.

Figure 5:
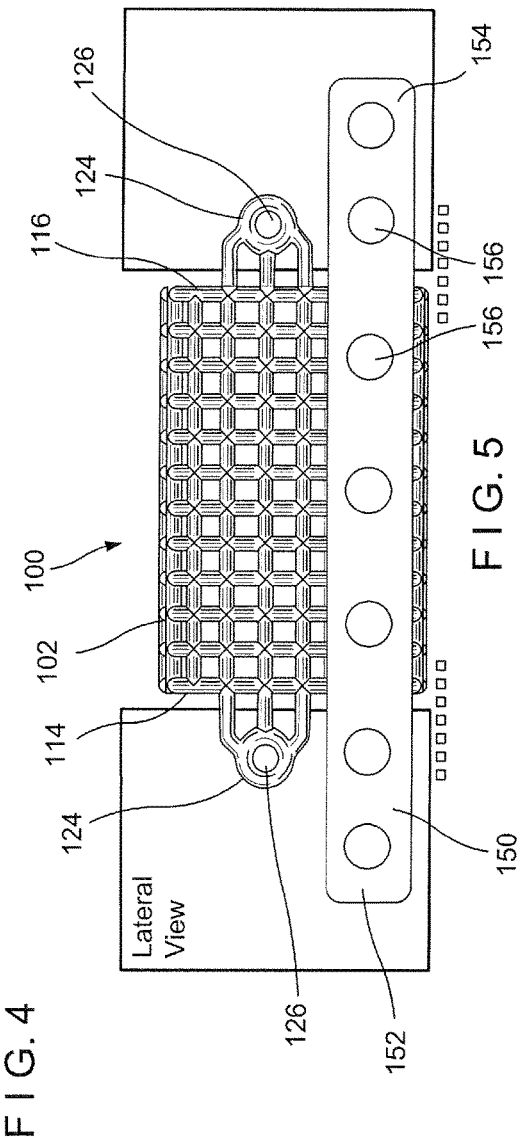
FIG. 5 shows a side view of the device of FIG. 1, in an operative position.

Once the 3D model has been adjusted, as desired, the custom, patient-specific graft containment device 100 is printed according to the adjusted 3D model. The channel 112 of the custom graft containment device 100 may be filled with a graft material and the custom device 100 positioned within the target space of the bone, as shown in FIG. 5. Fixation tabs 124 of the graft containment device 100 may extend over separated portions of the bone so that bone fixation elements inserted through the openings 126 of the fixation tabs 124 fix the custom device 100 to the bone. If so desired, as shown in FIG. 5, a fixation plate 150 may also be used to fix the graft containment device 100 to the bone. The fixation plate 150 may be positioned along the graft containment device 100 so that first and second ends 152, 154 thereof extend beyond the first and second ends 114, 116 of the body 102 to extend along separated portions of the bone. Bone fixation elements inserted through selected openings 156 of the fixation plate 150 fix the plate 150 both to the graft containment device 100 and to the bone. As described above, all of the pores 122 or pores 122 extending along a selected portion of the graft containment device 100 may be sized to receive bone fixation elements.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A method for treating a mandible, comprising:
    forming an initial digital 3D model of a mesh graft containment device based on dimensions of a target space of a mandible to be filled via the graft containment device, the 3D model of the graft containment device defined via a buccal surface, a lingual surface, a superior surface and an inferior surface;
    individually adjusting one of the buccal surface and the lingual surface relative to a first midplane, which extends through a longitudinal axis of the graft containment device between the buccal and lingual surfaces, to add or remove bulk along a desired portion of the 3D model of the graft containment device to form an adjusted 3D model; and
    forming a final graft containment device for placement in the target space of the mandible based on the adjusted 3D model.

2. The method of claim 1, further comprising individually adjusting one of the superior surface and the inferior surface relative to a second midplane, which extends through the longitudinal axis between the superior and inferior surfaces, to form the adjusted 3D model.

3. The method of claim 2, wherein adjusting one of the superior surface and the inferior surface includes adjusting one of a distance, a position and orientation of the one of the superior surface and the inferior surface relative to the second midplane.

4. The method of claim 1, wherein the dimensions of the target space of the mandible is obtained from an image scan of a patient.

5. The method of claim 1, wherein the adjusted 3D model is based on a desired treatment plan for a patient.

6. The method of claim 5, wherein the desired treatment plan includes planned future dental implants and the adjusted the 3D model includes added bulk along the lingual surface of the graft containment device.

7. The method of claim 1, further comprising adjusting a pore size of a portion of a body of the 3D model of the graft containment device to form the adjusted 3D model, pores along the portion of the body sized to receive bone fixation elements therethrough.

8. The method of claim 7, wherein the pore size is adjusted by adjusting a distance between one of adjacent circumferential members and adjacent longitudinal members, which define the mesh graft containment device.

9. The method of claim 1, wherein the initial 3D model includes a fixation tab extending from one of a first and second end of a longitudinally extending body of the graft containment device, the fixation tab including an opening extending therethrough to accommodate a bone fixation element for fixing the graft containment device to a portion of bone.

10. The method of claim 9, wherein the fixation tab extends from the buccal surface of the graft containment device.

11. The method of claim 9, further comprising adjusting the initial 3D model to include an additional fixation tab extending from the inferior surface of the graft containment device, the additional fixation tab including an opening extending therethrough to accommodate a bone fixation element for fixing the graft containment device to portion of bone.

12. The method of claim 1, wherein forming the final graft containment device includes three dimensionally printing the final graft containment device according to the adjusted 3D model.

13. The method of claim 1, wherein adjusting one of the buccal surface and the lingual surface includes adjusting one of a distance, a position and an orientation of the one of the buccal surface and the lingual surface relative to the first midplane.

14. The method of claim 1, further comprising adjusting a trajectory of the 3D model of the graft containment device.

* * * * *